United States Patent [19]

Magarinos et al.

[11] Patent Number: 4,802,719
[45] Date of Patent: Feb. 7, 1989

[54] INFRA-RED LASER SHIELD

[75] Inventors: Jose Magarinos; Daniel Coleman, both of Thornwood, N.Y.

[73] Assignee: Farrand Optical Co., Valhalla, N.Y.

[21] Appl. No.: 758,515

[22] Filed: Jul. 24, 1985

Related U.S. Application Data

[63] Continuation-in-part of Ser. No. 525,116, Aug. 22, 1983, abandoned, and a continuation-in-part of Ser. No. 639,661, Aug. 13, 1984.

[51] Int. Cl.$^4$ .................... G03H 1/04; G02B 5/32; G02C 7/10
[52] U.S. Cl. .................... 350/3.65; 350/3.7; 351/44
[58] Field of Search .................... 350/3.6, 3.65, 3.7, 350/3.81, 320; 351/44

[56] References Cited

U.S. PATENT DOCUMENTS

| | | | |
|---|---|---|---|
| 3,842,197 | 10/1974 | Broussand et al. | 350/3.65 X |
| 3,958,860 | 5/1976 | Breglia et al. | 350/3.65 |
| 4,447,111 | 5/1984 | Leib | 350/3.7 |
| 4,735,486 | 4/1988 | Leib | 350/3.7 X |

Primary Examiner—John K. Corbin
Assistant Examiner—David J. Edmondson
Attorney, Agent, or Firm—Handal & Morofsky

[57] ABSTRACT

A method of making a holographic optical element is disclosed. The method comprises the steps of determining the separation between interference pattern planes tangent to surfaces separated by a desired distance which achieves desired optical properties at a given first wavelength and angular orientation of light in a hologram disposed on a curved surface of first shape corresponding to the shape of a curved holographic element. The angular characteristics of exposure to achieve of this separation of planes in a planar analog of the desired curved holographic element is determined. The angles of exposure of interfering light rays to achieve this separation of planes in the planar analog by exposure of a sensitive substantially planar surface at a second wavelength in order to achieve the desired separation of planes and angular characteristics are determined. A source is constructed having the desired angular exposure characteristics and having a wavelength equal to the second wavelength, the source being constructed using a pair of source sets which are activated in sequence to make the desired interference pattern while shading parts of the substrate. An interference pattern is recorded in a photosensitive substantially planar film disposed on a substantially planar substrate using the constructed source. The interference pattern is developed. The developed interference pattern acts as a transmission hologram. The sensitive film with the interference pattern recorded in it is removed from the substantially planar substrate, the developing being done before removal of the sensitive layer in order that the removal may be carried out in a lighted area. The removed sensitive layer is the adhered to a substrate having the first shape, the removed layer being stretched and bent for adhesion to the substrate.

44 Claims, 4 Drawing Sheets

INFRA-RED LASER SHIELD

CROSS-REFERENCE TO RELATED APPLICATIONS

This application is a continuation in part of U.S. patent application Ser. No. 525,116, filed Aug. 22, 1983, now abandoned, directed to Ocular Protection Apparatus and naming Magarinos et al as inventors and a continuation in part of U.S. patent application Ser. No. 639,661, filed Aug. 13, 1984, directed to Ocular Protective Apparatus and naming Magarinos et al as inventors, which applications are incorporated herein by reference.

TECHNICAL FIELD

The present invention relates to an optical filter particularly useful for protecting an optical element or the human eye from laser hazards and exhibiting reflection and selectable optical geometric characteristics over a wide range of possible design wavelengths.

BACKGROUND OF THE INVENTION

The increasing use of laser light beams in military and other applications has underscored the need for protective systems and, particularly eye wear for protecting individuals from retinal damage. One method for dealing with this problem is the use of a conventional color filter coating on a pair of goggles worn by the individual. However, due to the fact that such filters filter out a wide range of wavelengths, the outside world tends to undergo drastic coloration when viewed through such a shield. In addition, if protection from a number of wavelengths is desired, the use of a multilayer conventional color filter reduces the quality of the system from marginal to unacceptable. Accordingly, attempts have been made to provide filters having extremely narrow bandstop regions.

A more desirable alternative to such conventional color filters is the holographic notch filter. Such notch filters, generally, have the desirable characteristic that upon being exposed with light of a given wavelength, in the proper holographic configuration, a very narrow bandwidth effectively reflective surface (which is optically a diffractive surface) will be formed holographically. This reflective surface or "notch filter" comprises recorded interference patterns in a photosensitive material such as dichromated gelatin. Such a holographically exposed gelatin layer will exhibit reflective properties along a very narrow range of wavelengths substantially identical to the recording wavelengths.

Such filters, however, have a disadvantage which stems from the fact that the interference pattern recorded in the gelatin layer during the holographic exposure process comprises a plurality of planes. When light is incident on the gelatin layer at an angle identical to that at which the layer was exposed, the incident light ray will experience the same distance between the planes. On the other hand, if light is incident at another angle, it will experience a distance between the planes which is somewhat greater or smaller than the separation between the layers. The distance between path distances between the planes at different angles of incident light is governed by trignometric relationships. Because the path distance varies, a holographically constructed notch filter adapted for use at a given angle will exhibit the desired notch reflective characteristics at different wavelengths for different angles.

While such devices have a wide range of possible useful applications, the above mentioned characteristic poses a serious problem in the event that one wishes to protect a small area object, such as the human eye from stray laser radiation emanating from a wide range of points on the horizon. In particular, if such a shield is placed in front of the eye, light directly in front of an individual would be reflected for light of a narrow range of wavelengths. On the other hand, light beams to the far right or left of the individual field of view will be reflected only for light of a different wavelength. In the case of laser hazards, the wavelengths are limited to a few discrete values which would be applied to the eye at a wide range of angles. Hence, a device such as that described above has only limited applications.

In our U.S. patent application Ser. No. 525,116 filed Aug. 22, 1983, the disclosure of which is incorpoated by reference, we described a system which removes some of the disadvantages of such earlier proposed systems. In particular, we proposed the construction of a holographic notch filter having a spherical optical configuration but whose actual shape may be flat or some other shape. The actual shape may be, for example, selected to be similar to ordinary spectacles. The optical spherical surface recorded in the gelatin layer is selected to have a center of curvature substantially coincident, in the typical case for spectacles, with the center of rotation of the eye of an individual. Thus, all light having the desired wavelength and traveling along a path which includes the user's eye will be normal to the optical surface when it passes through the gelatin layer and be will reflected.

However a serious limitation of such systems is the fact that dichromated gelatin is not sensitive to the various laser hazard wavelengths against which one desires to protect.

SUMMARY OF THE INVENTION

In principle, it is possible to vary the operating wavelength of a laser protective shield of the above type by exposing the filter at one wavelength and using it at another wavelength at an angle different from the recording angle. However, such a holographic construction requires a precise relationship between the recording wavelengths and the angles of recording incidence and the wavelengths and angles of incidence associated with use of the constructed holographic filter. While applicant's exposures of sectors in a spherical notch filter adapted to be used at or near the wavelengths of recording can, in principle, be recorded in multiple exposures of sectors in a substrate having any desired shape, including, a wrap-around or bug-eye protective goggle, the precise control of (1) recording, (2) optical geometry, and (3) physical shape with respect to desired wavelength and angles of use in such a system represents a difficult design problem as well as a cumbersome fabrication technique. In particular, in order for such a system to operate properly, light passing through the gelatin layer at a range of angles and defining a path which includes, for example, the eye of an individual, must be reflected. This can only be done by varying the angle of exposure from the angle of use in accordance with Bragg's law. If one considers Bragg's law and the consequent angles of exposure to achieve the desired spectral shift to enable the use of the notch filter at a wavelength other than the wavelength of exposure, one defines a relatively complex set of angles of exposure in order to achieve the desired results. If one considers such exposure on a curved or bug-eyed substrate, the problem becomes yet more complex. Indeed the only solution to this problem is the separate exposure of discrete portions of a protective shield with light having the desired wavelengths and angles of incidence. In view of the complexity of such a solution, one is invariably directed toward the use of a recording made at or near the wavelengths against which protection is desired. However, in the case of red or near infrared or other laser wavelengths at which protection may be desired, the sensitivity of dichromated gelatin is very attenuated or substantially nonexistent. Thus exposure of such a device is not practical in accordance with prior art techniques.

In accordance with the present invention, the above-identified problem is eliminated by simplifying the exposure requirements of the shield. In accordance with a preferred embodiment of the invention, protection of two eyes is achieved through the use of complementary symmetrical notch filters, through the inventive recording, and redevelopment operation.

BRIEF DESCRIPTION OF DRAWINGS

Several ways of carrying out the method of the present invention are discussed in detail below with reference to the drawings, in which.

DETAILED DESCRIPTION

Figure 1:
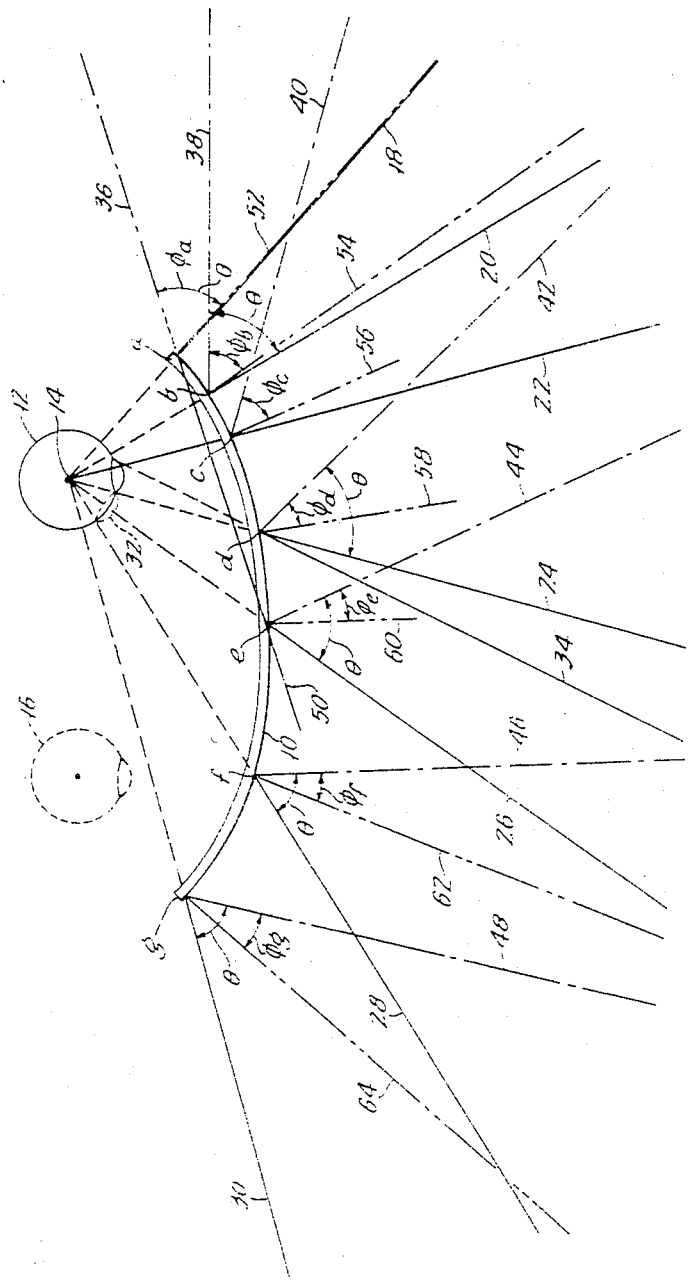
FIG. 1 is a diagram illustrating the optical properties of a protective laser element.

As a starting point let us consider the optical geometries of the desired finished product. Such a product may comprise an ocular protection shield 10, as illustrated in FIG. 1. Such a shield would be used to protect one eye 12 of the user from harmful radiation traveling toward the center 14 of the eye. For purposes of analysis we will, at first, ignore eye 16.

One can consider dangerous radiation to be various rays of light 18, 20, 22, 24, 26, 28, and 30 incident on the transparent shield and heading toward the center 14 of eye 12. If we consider that, for a given shield, we are concerned with only one harmful wavelength of radiation, one would need a shield in which light of that wavelength incident along the paths defined by rays 18-30 would be reflected for a very narrow bandwidth centered on the harmful wavelength.

As discussed in our earlier application, noted above, the narrower the bandwidth of such a filter, the smaller the range of angles over which the harmful wavelength will be reflected and, most desirably, the less the coloration of the outside world as viewed by eye 12. Thus, theoretically, one might want the narrowest range of angles of reflection for the harmful wavelength that can be tolerated given the angular difference of light incident on different parts of the lens 32 of the eye at its various positions. This is illustrated in FIG. 1 by incident light ray 34 which, while it is not heading toward the center of rotation of the eye, is aimed at the periphery of the lens 32 of the eye thus causing its angle to be slightly deviated from the ray 24 which is aimed toward the center of the eye. Thus, notches with an infinitely small band-reflection characteristics would not be practical in, for example, an ocular protection system.

For purposes of explanation, we will, however, at first only consider the characteristics of rays aimed toward the center 14 of eye 12. Generally, if it is desired to provide ocular protection against light of a given wavelength, it is necessary to construct a holographic mirror in a light sensitive film deposited on the surface of shield 10 using a point source positioned at center 14 and having the same wavelength as the wavelength against which protection is desired. If such a construction were made, light rays 18-30 of the same given wavelength would be reflected, while other wavelengths would be allowed to pass thus giving a relatively un-colored picture of the outside world to eye 12.

The limitation which presents itself, however, is the insensitivity of known holographic emulsions to a number of wavelengths which correspond to harmful radiation. However, due to the fact that fabrication of a holographic reflector at one angle will result in narrow bandwidth reflective properties at other angles, but for different wavelengths, it is possible to construct holographic notch filters, using such angular exposures, at a wide range of laser frequencies.

In particular, for any desired angle of incidence with respect to a planar surface, it is possible to calculate the distance between the planes of interference patterns required for reflection. For example, if one desires to reflect light incident at an angle $\theta$ and of wavelength w, at which an emulsion is insensitive, one may solve for the distance d between the planes for reflection at a given angle with respect to the plane, using Bragg's law:

$$w = 2nd \sin \theta,$$

where n is the index of refraction of the sensitive holographic emulsion deposited on a substrate.

Once the distance d between planes in the interference pattern which one desires to create has been calculated using Bragg's law, as discussed above, one may solve for the angle of exposure for the same distance d between the planes in the intereference pattern given a particular laser wavelength at which the emulsion is sensitive. One then solves for the angle of exposure $\theta_e$ given the wavelength $w_e$ of the laser source at which the holographic emulsion is sensitive, the index of refraction of the emulsion and the distance between the planes calculated above using Bragg's law $w_e = 2nd \sin \theta_e$, where $w_e$ is the wavelength of light at which the photographic holographic emulsion is sensitive.

Once one has calculated the angular difference between the angle of exposure of the hologram at one wavelength and the angle of use of the hologram at another wavelength, it then becomes necessary to select a source at the exposure wavelength having the desired angular characteristics.

In principle, such a holographic recording technique is applicable to a curved shield such as shield 10 in FIG. 1. In particular, considering light rays 18-30, against which one wishes to protect the eye of the user, it would become necessary to expose the shield at a different angle for each point depending upon the angular orientation of the rays 18-30 against which one wishes to protect eye 12. In particular, if we consider an angular deviation θ, we would construct exposure rays 36–48. However, such a holographic construction requires a relatively complex exposure source. For example, if one considers a light ray passing along the path defined by exposure ray 36, it would follow a path defined by line 50 which, obviously, passes through the sensitive layer before exposing point a through which harmful ray 18 passes. Obviously, this poses a serious problem. Thus, perhaps, the only solution for exposure of each point on shield 10, such as points a–g, is to individually expose each area separately with a light beam having the orientation of rays 36–48. Unfortunately, such a construction would still only be an approximation and would require a large number of exposures.

In accordance with the invention this is made unnecessary by considering first the angles of incidence of exposure light rays 36–48 with respect to normals 52–64. In particular, we note that recording or exposure light rays 36–48 have angles to the normal $\phi_a$, $\phi_b$, $\phi_c$, $\phi_d$, $\phi_e$, $\phi_f$, and $\phi_g$. As can be seen from inspection of FIG. 1, the angles of recording with respect to the normal, just as the angles or recording rays 36–48 vary in a relatively complicated fashion.

Figure 2:
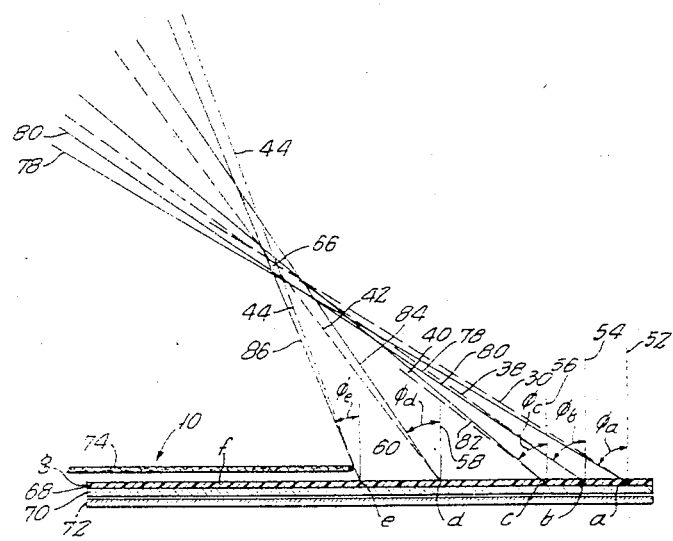
FIGS. 2-3 illustrates construction geometry for the shield of FIG. 1.

If we consider a flattened analog of the shield 10, we would have a structure such as that illustrated in FIG. 2. If we consider the normals 52–64, they will all be normal to the flattened out shield 10 and, accordingly, parallel to each other. If we then reconstruct recording rays 36–44 they would have the general orientations illustrated in solid lines in FIG. 2. It is noted that these rays generally define an average point of intersection, illustrated as point 66. These rays, in a hologram recording configuration, approximate a theoretcal point source and, in fact, can be approximated by a real point source.

Thus, if one wishes to create a holographic notch filter having the characteristics illustrated on the right side of normal 60, one deposits a thin layer of photosensitive material 68 on a substrate 70. One then places a mirror 72 behind sensitive layer 68. A point source is then placed at point 66 and a shade 74 placed over the left half of the sensitive layer 68. The point source is then illuminated to expose the right half of the sensitive layer 68 with the light rays 78–86.

In similar fashion, one considers also the left half of the sensitive layer 68 which, in the flattened state defines recording light rays 44–48. Similar to the construction illustrated in FIG. 2, as is illustrated most clearly in FIG. 3, these light rays, respectively, will define with respect to normals 60, 62, and 64, angles $\phi_e$, $\phi_f$, and $\phi_g$. Likewise, the rays striking points e, f and g may be approximated by a point source positioned at point 75. Thus, the left half of the hologram would be exposed by placing a point source at point 75, a shade 76 over the right half of the shade 10 and a mirror 78 behind the sensitive layer 68.

Figure 3:
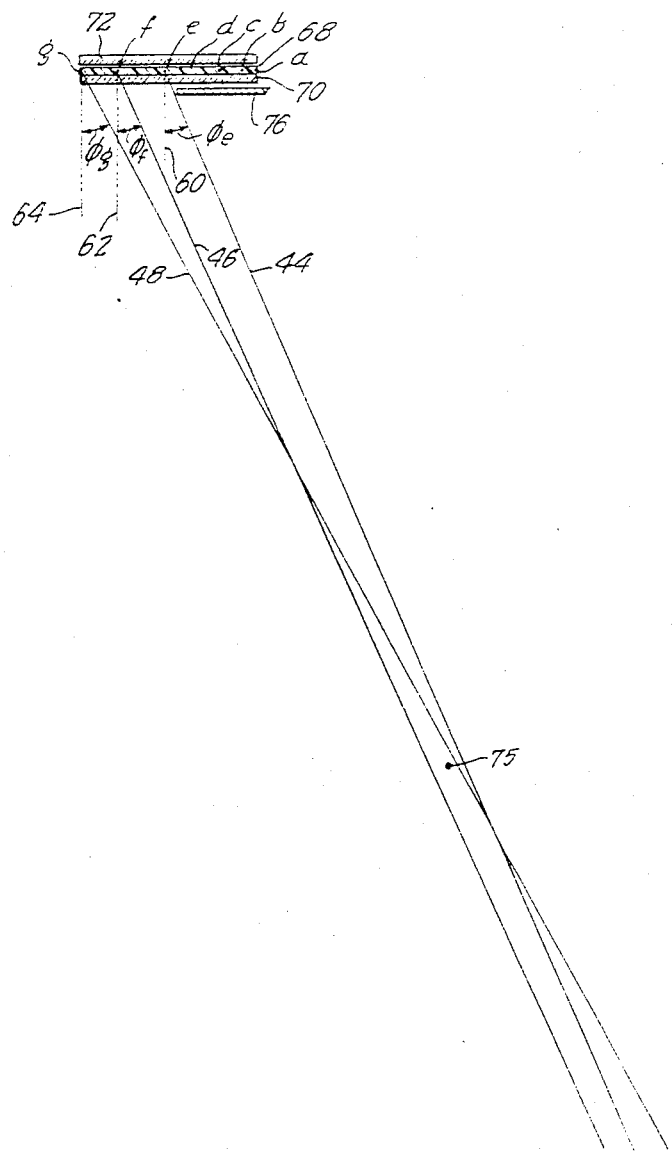

The point source exposures made as shown in FIGS. 2 and 3, although they represent appoximations of the ideal, are sufficient to make a commercially acceptable product. In particular, it is noted that the notches have a relatively narrow but very real range of angular reflectivity for a given wavelength. Thus if the deviations between the theoretical recording ray paths 36–44, in FIG. 2 are angularly only slightly deviated from the actual recording paths 78–86, acceptable operation can be achieved. The same constraints apply to the exposure illustrated in FIG. 3.

After the flat holograms has been exposed as illustrated in FIGS. 2–3, the light sensitive emulsion 68 must be photographically developed and washed, and, if desired, fixed and washed. As soon as this is completed the finished hologram may be dried. The next step in the inventive process is the transfer of the hologram manufactured on a flat glass substrate from the glass substrate 70 to a curved substrate which conforms essentially to the physical configuration of shield 10. Transfer of the film is achieved by re-wetting the finished hologram. This effectively eliminates the desirable properties of the hologram. The wetting of the finished dried hologram on the flat substrate can be carried out using water or any suitable photographic film wetting agent. After the developed gelatin layer has been removed from the substrate, it is not only flexible but will exhibit a certain degree of stretch. Thus it can be draped over cylindrically shaped substrates as well as spherical or other substrates which are curved in two orthogonal directions. A razor blade is used to assist the peeling of the hologram formed in the gelatin layer, from the glass substrate.

Once the gelatin layer which comprises a holographically exposed sensitive layer 68 is removed from the substrate, it may be transferred, while wet, to a substrate which generally has the configuration illustrated in FIG. 1. Because the gelatin is still wet, it naturally adheres to the curved substrate and together with the curved substrate forms the shield 10. However, the sensitive layer 68 no longer has a hologram recorded in it. The interference pattern is eliminated by the wetting process. However, after the sensitive gelatin layer 68 has been allowed to dry on the substrate after transfer, the hologram may be developed normally and returns with a commercially acceptable characteristic.

After the transfer of the hologram has been achieved, the resulting shield has, effectively, the same operating characteristics as the theoretically exposed shield exposed with individual discrete rays over its entire surface as was discussed above in connection with FIG. 1.

The finished shield has the characteristic that light at a given wavelength different from the wavelength of exposure during the steps illustrated in FIGS. 2 and 3, if incident along the paths defined by light rays 18–30 will be reflected, while light rays of wavelengths different from the desired wavelength of reflection will pass through to the eye giving an only slightly colored picture of the outside world.

In the manufacture of a practical shield 10, it is desirable also to protect eye 16 from harmful radiation. This is achieved by exposing a second flat hologram with the two step process illustrated in FIG. 2 and 3 with the exception that the exposure is opposite to and symmetrical about normal 60, thus providing a mirror image of the characteristic illustrated with respect to eye 12 in FIG. 1. The second hologram is then developed, fixed, dried, and then re-wetted and removed and disposed over the first substrate. The two overlying laminated substrates then provide a protection characteristic for two eyes.

Figure 4:
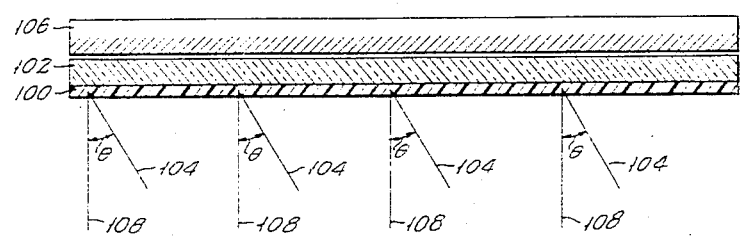
FIGS. 4 and 5 illustrate the construction and optical characteristics of an alternative optical element constructed in accordance with the present invention.

Construction of another optical element in accordance with the present invention is illustrated in FIG. 4. Initially a sensitive layer 100 is deposited on a substrate 102. Collimated light rays 104 are used to expose sensitive layer 100 while interfering with their own reflections reflected by a mirror 106 disposed on the opposite side of the substrate 102. The then finished film, exposed at one wavelength with light rays 104 will at a constant angle θ (calculated in accordance with Bragg's law) with respect to the angle of exposure define a reflective surface to light rays travelling along, for example, normals 108.

Figure 5:
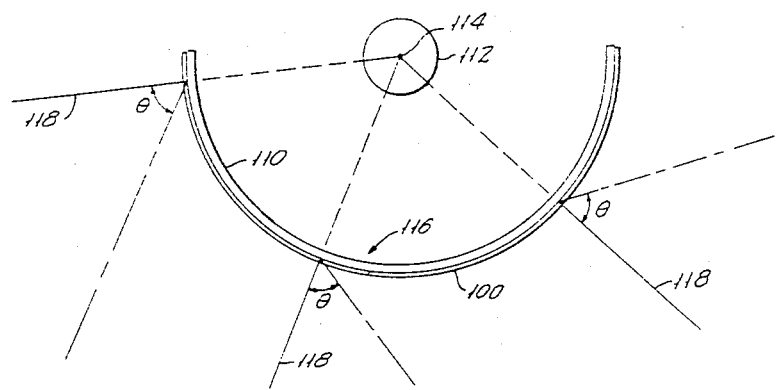

The exposed gelatin layer 100 is then developed, fixed, dried, and re-wetted and then removed from substrate 102 and adhered to, in the illustrated example, a concave substrate 110 illustrated in FIG. 5. Because the gelatin layer, when wet can be stretched, substrate 110 may be curved in two orthogonal directions. For example it may be spherical. Thus an element 112 which one desires to protect may be placed in the position illustrated in FIG. 5, an imaginary line starting from its center 114, coinciding with normals to the surface of shield 116 and, more particularly, normals to the remounted gelatin layer 100. This remounted gelatin layer, once it has been dried, will again exhibit the desired reflective characteristics to light rays 118 impinging upon it along a path defined by imaginary lines passing through the center 114 of element 112, which one desires to protect.

Figure 6:
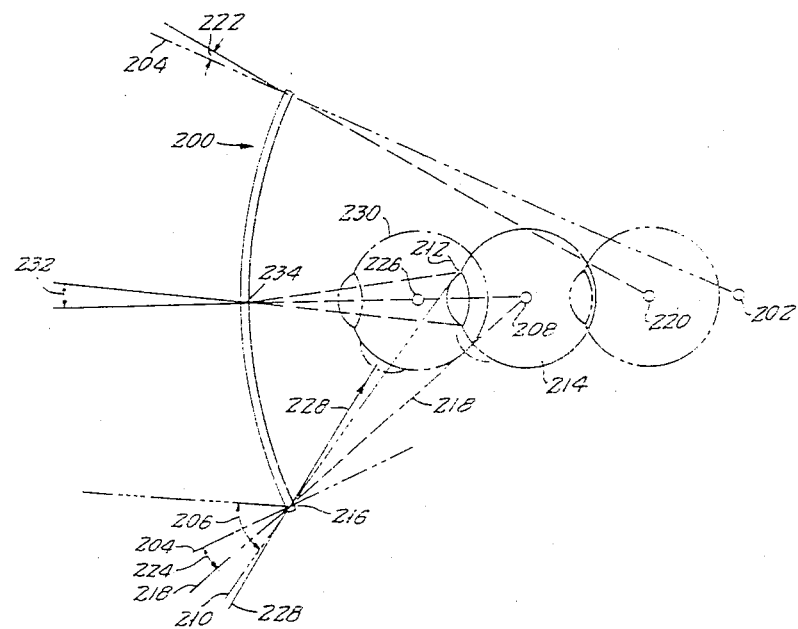
FIGS. 6 illustrates possible configurations of use and characteristics of an optical element such as that manufactured in accordance with FIGS. 4-5.

As can be understood with reference to FIG. 6, it is not necessary that an eye or any element which one desires to protect be centered with its center rotation coincident with the center curvature of a spherical mirror. In particular, one could consider a spherical mirror 200 comprising a small section of a spherical surface manufactured in accordance with FIGS. 4-5 and having an optical center of curvature at point 202. Thus, point 202 will define normals 204 along which reflection will occur at the desired wavelength. However, because reflections for the desired wavelength will occur about a range of angles, this range of angles being illustrated by angle 206, it is possible for an eye to be protected if it is centered about point 208. For example, a light ray 210 which is headed toward a point 202 at the periphery of the lens of eye 214 will be within the range of reflection defined by angle 206 at point 216 on the shield mirror 200.

Likewise, a light ray heading through point 216 and aimed at center 208 will follow the path illustrated by line 218, but because it is within the range of reflection will be reflected, protecting the eye from harm.

It is well known in the art that, depending upon the emulsion composition, and the method of application of the emulsion and development, the bandwidth of a notch may be varied. If one desires less coloration than would be provided by the protective system illustrated for eye 214 in FIG. 6, a narrower bandwith emulsion could be used. However, in order for such a system to be effective the position of the center of the eye to be protected would have to be further back, for example, coincident with point 220. In this case the range and angle defined at the periphery of the lens would be relatively small as is indicated by angle 222. It is noted that angle 222 is substantially smaller than its corresponding angle 224 in the previously described example. On the other hand, if an eye were positioned at point 226, the reflective notch filter contained in shield 200 would not protect it from harmful radiation inasmuch as light rays 228 impinging upon the surface of shield 200 would be outside the widest angular range for reflection 206 defined by the earlier example and would pass to the lens of an eye 230 centered on point 226.

The critical case for such devices is at the periphery of the lens of the eye at extremes of lens postion due to eye rotation, and at the periphery of shield 200. In particular, the angle of reflection 232 when considered with respect to the center 234 of the spectacle lens, as illustrated in FIG. 6, is far less than the range of angular rejection required at the periphery and indicated by reference numeral 206.

It is noted that the stretching process may change the distance between the planes if it is very great in magnitude. In particular, stretching of a layer with a diffraction grating in it will result in decreasing the separation between the various layers. This effect, however, even under great stretching, causes about a ten percent change in separation although, theoretically, greater changes in separation would be possible if film could be made to stretch more. The effect of this stretch may be measured and incorporated in later hologram constructions so as to fine tune the final product to operate optimally at the desired wavelength.

Finally, another alternative is the transfer of a dried exposed photosensitive layer. Also, the photosensitive layer can also be disposed on a bendable and/or oven stretchable substrate, which may be directly bent and for streched, and adhered to a curved substrate without peeling.

While preferred embodiments of the invention have been described, various modifications may be apparent to those of ordinary skill in the art. For example, the exposed developed and fixed photosensitive layer may be peeled before drying and directly transferred to a curved substrate. Such modifications are within the spirit and scope of the invention which is limited and defined only by the appended claims.

We claim:

1. A method for making a holographic optical element, comprising the steps of:
    (a) calculating a parameter related to the separation between interference pattern surfaces tangent to surfaces separated by a distance which achieves desired optical properties at a given first wavelength and angular orientation of light in a hologram disposed in a curved first shape corresponding to the shape of a curved holographic element;
    (b) calculating the angular characteristics of exposure, at a second wavelength to achieve said separation of planes in the desired curved holographic element;
    (c) calculating angles of exposure of interefering light rays to achieve said separation in an analog of second shape of said curved holographic element by exposure of a sensitive surface of said second shape at a wavelength equal to said second wavelength in order to achieve the desired separation;
    (d) constructing a source having substantially the desired angular exposure characteristics and having a wavelength equal to said second wavelength, said constructed source comprising two sources;
    (e) activating said sources to make a desired interference pattern to record an interference pattern in a photosensitive film having said second shape using said constructed source and a mirror positioned on the side of said film opposite said sources;
    (f) developing said interference pattern, the developed interference pattern acting as a transmission hologram;
    (g) removing the sensitive film with the inteference pattern recorded in it from said substrate; and
    (h) changing the shape of and causing the removed sensitive film to be adhered to a substrate of said first shape.

2. A method as in claim 1, wherein said developing is done before removal of the sensitive layer in order that said removal may be carried out in a lighted area.

3. A method of making a holographic optical element, comprising the steps of:
   (a) recording an interference pattern in a sensitive film disposed on a substrate having a first shape;
   (b) developing said interference pattern;
   (c) removing the sensitive film from the substrate with the interference pattern recorded in it; and
   (d) adhering the removed sensitive layer to a substrate having a second shape.

4. A method as in claim 3, wherein said sensitive film is photo sensitive and said interference pattern consists of light energy.

5. A method as in claim 4, wherein said recording is carried out in said sensitive layer while it disposed on said first shape which is substantially planar and said adhering is carried out onto said second shape which is curved.

6. A method as in claim 5, wherein said adhesion is made to a spherical surface.

7. A method as in claim 4, wherein said interference pattern acts as a reflective hologram.

8. A method as in claim 4, wherein said interference pattern acts as a transmission hologram.

9. A method as in claim 4, wherein said removed layer is streched and bent to a desired shape for adhesion to said substrate.

10. A method as in claim 9, wherein said recording is carried out in said sensitive layer while it is disposed in said first shape which is substantially planar and said adhering is carried out onto said second shape which is curved.

11. A method as in claim 4, wherein said developing comprises separate photographic development and fixing steps.

12. A method as in claim 11, wherein said source is constructed using a pair of individual sources which are activated in sequence to make interference patterns while shading different parts of the substrate.

13. A method as in claim 12, wherein said removed layer is streched and bent to a desired shape for adhesion to said substrate.

14. A method as in claim 3, wherein said developing is done before removal of the sensitive layer in order that said removal may be carried out in a lighted area.

15. A method as in claim 14, wherein said recording is carried out in said sensitive layer while it is disposed on said first shape which is substantially planar and said adhering is carried out onto said second shape which is curved.

16. A method of making a holographic optical element, comprising the steps of:
   (a) determining the desired optical properties at a given first wavelength and angular orientation of light in a hologram disposed on a curved surface of first shape corresponding to the shape of said curved holographic element for a group of points on said holographic element, said optical properties dictating the separation between interfering optical surfaces in said holographic element;
   (b) determining the angular characteristics of a planar analog of said desired curved holographic element at said first wavelength;
   (c) determining angles of exposure of interfering light rays of a second wavelength to achieve said separation in said flat analog by exposure of a sensitive substantially planar surface at a second wavelength in order to achieve the desired separation of planes and angular characteristics;
   (d) constructing a source having the desired angular exposure characteristics and having a wavelength equal to said second wavelength;
   (e) recording an interference pattern in a photosensitive substantially planar film disposed on a substantially planar substrate using said constructed source;
   (f) developing said interference pattern;
   (g) removing the sensitive film with the interference pattern recorded in it from said substantially planar substrate; and
   (h) adhering the removed sensitive layer to a substrate having said first shape.

17. A method as in claim 16, wherein said source is constructed using a pair of individual sources which are each activated in sequence to make the desired interference pattern in a part of the film.

18. A method as in claim 16, wherein said adhesion is made to a spherical surface.

19. A method as in claim 16, wherein said interference pattern acts as a transmission hologram.

20. A method as in claim 16, wherein said developing is done before removal of the sensitive layer in order that said removal may be carried out in a lighted area.

21. A method as in claim 16, wherein said removed layer is streched and bent for adhesion to said substrate.

22. A method of making a curved holographic optical element, comprising the steps of:
   (a) determining desired optical properties at a given first wavelength and angular orientation of light in a hologram disposed on a curved surface of first shape corresponding to the shape of said curved holographic element for a group of points on said holographic element, said optical properties dictating the separation between interfering optical surfaces in said holographic element;
   (b) determining the angular characteristics of a flat analog of said desired curved holographic element at said first wavelength;
   (c) determining for each of said points the angles of exposure of interfering light rays of a second wavelength to achieve said separation in said flat analog by exposure of a sensitive substantially planar surface at a second wavelength in order to achieve the desired separation of planes and angular characteristics;
   (d) constructing a source having the desired angular exposure characteristics and having a wavelength equal to said second wavelength;
   (e) recording an interference pattern in a photosensitive substantially planar bendable film disposed in a substantially planar configuration using said constructed source;
   (f) developing said interference pattern;
   (g) bending the sensitive film with the interference pattern recorded in it to conform to a substrate having said first shape; and
   (h) adhering the sensitive film to said substrate having said first shape.

23. A holographic optical element, made by the method comprising the steps of:
   (a) determining the separation between interference pattern planes tangent to surfaces separated by a distance which achieves desired optical properties at a given first wavelength and angular orientation of light in a hologram disposed on a curved surface of first shape corresponding to the shape of a curved holographic element;
(b) determining the angular characteristics of exposure to achieve said separation of planes in the desired curved holographic element;
(c) determining angles of exposure of interfering light rays to achieve said separation of planes in a planar analog of said curved holographic element by exposure of a sensitive substantially planar surface at a second wavelength in order to achieve the desired separation of planes;
(d) constructing a unitary source having the desired angular exposure characteristics and having a wavelength equal to said second wavelength, said unitary source being constructed using a pair of sources;
(e) activating said sources to make the desired interference pattern each of said sources exposing a respective part of the substrate to record an interference pattern in a photosensitive substantially planar film disposed on a substantially planar substrate using said source;
(f) developing said interference pattern, the developed interference pattern acting as a transmission hologram;
(g) changing the shapes of said planar film.

24. An optical element as in claim 22, wherein said shape changing is done by:
(h) removing the sensitive film with the interference pattern recorded in it from said substantially planar substrate, said developing being done before removal of the sensitive layer in order that said removal may be carried out in a lighted area; and
(i) adhering the removing sensitive layer to a substrate having said first shape, said removed layer being stretched and bent to a desired shape for adhesion to said substrate.

25. A holographic optical element made by the method comprising the steps of:
(a) recording an interference pattern in a sensitive film disposed on a substrate having a first shape;
(b) developing said interference pattern;
(c) removing the sensitive film from the substrate with the interference pattern recorded in it; and
(d) adhering the removed sensitive layer to a substrate having a second shape.

26. A holographic element as in claim 25, wherein said sensitive film is photosensitive and said interference pattern consists of light energy.

27. A holographic element as in claim 26, wherein said recording is carried out in said sensitive layer while it is disposed on said first shape which is substantially planar and said adhering is carried out onto said second shape which is curved.

28. A holographic element as in claim 27, wherein said adhesion is made to a spherical surface.

29. A holographic element as in claim 26, wherein said interference pattern acts as a reflective hologram.

30. A holographic element as in claim 26, wherein said interference pattern acts as a transmission hologram.

31. A holographic element as in claim 26, wherein said removed layer is streched and bent to a desired shape for adhesion to said substrate.

32. A holographic element as in claim 31, wherein said recording is carried out in said sensitive layer while it is disposed in said first shape which is substantially planar and said adhering is carried out onto said second shape which is curved.

33. A holographic element as in claim 26, wherein said developing comprises separate photographic development and fixing steps.

34. A holographic element as in claim 33, wherein said source is constructed using a pair of individual sources which are activated in sequence to make interference patterns while shading different parts of the substrate.

35. A holographic element as in claim 34, wherein said removed layer is stretched and bent to a desired shape for adhesion to said substrate.

36. A holographic element as in claim 25, wherein said developing is done before removal of the sensitive layer in order that said removal may be carried out in a lighted area.

37. A holographic element as in claim 36, wherein said recording is carried out in said sensitive layer while it is disposed on said first shape which is substantially planar and said adhering is carried out onto said second shape which is curved.

38. A curved holographic optical element made by the method comprising the steps of:
(a) determining desired angular optical properties at a given first wavelength and angular orientation of light in a hologram disposed on a curved surface of first shape corresponding to the shape of said curved holographic element for a group of points on said holographic element, said optical properties dictating the separation between interfering optical surfaces in said holographic element at each of said points;
(b) determining the angular optical properties of a flat analog of said desired curved holographic element at said first wavelength;
(c) determining for each of said points the angles of exposure of interfering light rays of a second wavelength to achieve said separation in said flat analog by exposure of a sensitive substantially planar surface at a second wavelength in order to achieve the desired separation of planes and angular properties;
(d) constructing a source having the desired angular exposure characteristics and having a wavelength equal to said second wavelength;
(e) recording an interference pattern in a photosensitive substantially planar film disposed on a substantially planar substrate using said constructed source;
(f) developing said interference pattern;
(g) removing the sensitive film with the interference pattern recorded in it from said substantially planar substrate; and
(h) adhering the removed sensitive layer to a substrate having said first shape.

39. A holographic element as in claim 38, wherein said source is constructed using a pair of individual sources which are each activated in sequence to make the desired intereference pattern in a part of the film.

40. A holographic element as in claim 38, wherein said adhesion is made to a spherical surface.

41. A holographic element as in claim 38, wherein said interference pattern acts as a transmission hologram.

42. A holographic element as in claim 38, wherein said developing is done before removal of the sensitive layer in order that said removal may be carried out in a lighted area.

43. A holographic element as in claim 38, wherein said removed layer is streched and bent for adhesion to said substrate.

44. A curved holographic optical element, made by the method comprising the steps of:
  (a) determining desired optical properties for light with a given pattern of angular orientation in a hologram disposed on a surface of first shape corresponding to the shape of said curved holographic element for a group of points on said holographic element, said optical properties dictating the separation between diffracting optical surfaces in said holographic element;
  (b) determining the angular characteristics of an exposure source to achieve said desired optical properties;
  (c) determining angular characteristics of interfering light rays necessary to achieve said optical properties in an analog of second shape by exposure of a sensitive surface of said second shape in order to achieve the desired separation of diffracting surfaces in said first shape after deformation into said second shape;
  (d) constructing a source having the desired angular exposure characteristics;
  (e) recording an interference pattern in a photosensitive bendable film disposed in said second shape using said constructed source;
  (f) developing said interference pattern; and
  (g) bending the sensitive film with the interference pattern recorded in it to conform to said first shape.

* * * * *